United States Patent [19]

Putnam et al.

[11] Patent Number: 5,580,852
[45] Date of Patent: Dec. 3, 1996

[54] DERIVATIVES OF TACHYPLESIN HAVING INHIBITORY ACTIVITY TOWARDS PLANT PATHOGENIC FUNGI

[75] Inventors: Rebecca J. Putnam, West Des Moines; A. Gururaj Rao, Urbandale, both of Iowa

[73] Assignee: Pioneer Hi-Bred International, Inc., Des Moines, Iowa

[21] Appl. No.: 168,809

[22] Filed: Dec. 17, 1993

[51] Int. Cl.$^6$ ............... A01N 25/00; A01N 63/02; C07K 7/00
[52] U.S. Cl. ............... 514/2; 47/58; 424/405; 530/326
[58] Field of Search ............... 800/200, 205, 800/250, 255, DIG. 9, 52, 56; 935/18; 435/172.1, 172.3, 240.4; 530/333, 326; 47/58; 424/418; 514/2, 13

[56] References Cited

FOREIGN PATENT DOCUMENTS

| | | | |
|---|---|---|---|
| 0320130A2 | 6/1989 | European Pat. Off. | A01N 63/04 |
| 0497366 | 1/1992 | European Pat. Off. | |
| 0502718 | 3/1992 | European Pat. Off. | |
| 0513613 | 5/1992 | European Pat. Off. | |
| 0545730A1 | 6/1993 | European Pat. Off. | A01N 63/02 |
| WO8904371 | 5/1989 | WIPO | C12P 21/00 |
| 9011771 | 4/1990 | WIPO | |

OTHER PUBLICATIONS

Kawano, et al. (1990) Antimicrobial Peptide, Tachyplesin I, Isolated From Hemocytes of the Horseshoe Crab (*Tachypleus tridentatus*), *The Journal of Biological Chemistry*, vol. 265, No. 26, pp. 15365–15367.

Masuda, et al. (1992) A Novel Anti–HIV Synthetic Peptide, T-22[TYR$^{5, 12}$, LYS$^7$ –Polyphemusin II), *Biochemical and Biophysical Research Communications*, vol. 189, No. 2, pp. 845–850.

Matsuzaki, et al. (1991) Interactions of an antimicrobial peptide, tachyplesin I, with lipid membranes, *Biochimica et Biophysica Acta*, pp. 259–264.

Miyata, et al. (1989) Antimicrobial Peptides, Isolated from Horseshoe Crab Hemocytes, Tachyplesin II, and Polyphemusins I and II: Chemical Structures and Biological Activity, *J. Biochem*, vol. 106, No. 4, pp. 663–668.

Muta, et al. (1990) Tachplesins Isolated from Hemocytes of Southeast Asian Horseshoe Crabs (*Carcinoscorpius rotundicauda* and *Tachyplesin gigas*): Identification of a New Tachyplesin, Tachyplesin III, and a Processing Intermediate of its Precursor, *J. Biochem.*, vol. 108, No. 2, pp. 261–266.

Nakamura, et al. (1988) Tachyplesin, a Class of Antimicrobial Peptide from the Hemocytes of the Horseshoe Crab (*Tachypleus tridentatus*), *The Journal of Biological Chemistry*, vol. 263, No. 32, pp. 16709–16713.

Ohta, et al. (1992) Mechanisms of Antibacterial Action of Tachyplesins and Polyphemusins, a Group of Antimicrobial Peptides Isolated from Horseshoe Crab Hemocytes, *Antimicrobial Agents and Chemotherapy*, vol. 36, No. 7, pp. 1460–1465.

Park, et al. (1992) Conformation of Tachyplesin I from *Tachypleus tridentatus* When Interacting with Lipid Matrices, *Biochemistry*, vol. 31, No. 48, pp. 12241–12247.

Shieh, et al. (1989) Synthesis and properties of tachyplesin I, a lipospolysaccharide–binding peptide, from *Tachypleus tridentatus*, *Febs Letters*, vol. 252, No. 1, 2, pp. 121–124.

Shigenaga, et al. (1990) Antimicrobial Tachyplesin Peptide Precursor, *The Journal of Biological Chemistry*, vol. 265, No. 34, pp. 21350–21354.

Tamamura, et al. (1993) A comparative study of the solution structures of tachyplesin I and a novel anti–HIV synthetic peptide, T22[Tyr$^{5, 12}$, Lys$^7$]-polyphemusin II), determined by nuclear magnetic resonance, *Biochimica et Biophysica Acta*, pp. 209–216.

Tamamura, et al. (1993) Antimicrobial Activity and Conformation of Tachyplesin I and Its Analogs, *Chem. Pharm. Bull.*, vol. 41, No. 5, pp. 978–980.

Yonezawa, et al. (1992) Binding of Tachyplesin I to DNA Revealed by Footprinting Analysis: Significant Contribution of Secondary Structure to DNA Binding and Implication for Biological Action, *Biochemistry*, vol. 31, pp. 2998–3004.

Tamamura, et al. (1993) Anti–HIV Activity and Conformational Analysis of a Novel Synthetic Peptide, T22 ([TYR$^{5, 12}$, LYS$^7$]-Polyphemusin II), *Thirteenth American Peptide Symposium, Abstracts*, p. 2–96.

Finnegan et al. 1994. Bio/Technology. 12:883–888.

Potrykus. 1991. Annu. Rev. Plant Physiol. Plant Mol. biol. 42:205–225.

Sambrook et al. 1989. Molecular Cloning–A Laboratory Manual. 2nd Ed. pp. 11.2–11.19, 11.45–11.49, and 11.52–11.61.

Gordon–Kamm et al. 1990. The Plant Cell. 2:603–618.

*Primary Examiner*—Erich E. Veitenheimer
*Attorney, Agent, or Firm*—Pioneer Hi-Bred International, Inc.

[57] ABSTRACT

Certain specific derivatives of the 17-amino acid peptide tachyplesin has been found to have antimicrobial activity against plant pathogens. In a preferred embodiment, plant resistance to diseases caused by plant pathogens which are susceptible to these peptides is produced by inserting into the cells of a plant a gene whose expression causes production of one or more of the peptides of this invention in the plant in antimicrobial amounts.

6 Claims, No Drawings

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

```
Lys  Trp  Leu  Phe  Arg  Val  Asn  Gly  Ser  Ser  Gly  Lys  Tyr  Arg  Arg  Gln
1                  5                          10                         15
Arg
```

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Lys  Trp  Leu  Phe  Arg  Val  Asn  Phe  Arg  Gly  Ile  Lys  Tyr  Arg  Arg  Gln
1                  5                          10                         15
Arg
```

( 2 ) INFORMATION FOR SEQ ID NO:3:

( i ) SEQUENCE CHARACTERISTICS:
        ( A ) LENGTH: 17 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:3:

Lys Trp Leu Phe Arg Val Asn Gln Leu Met Phe Lys Tyr Arg Arg Gln
1               5                   10                  15
Arg (2) INFORMATION FOR SEQ ID NO:4:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:4:

Lys Trp Cys Phe Arg Val Cys Tyr Arg Gly Ile Cys Tyr Arg Arg Cys
1               5                   10                  15
Arg (2) INFORMATION FOR SEQ ID NO:5:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

Lys Trp Ala Phe Arg Val Ala Tyr Arg Gly Ile Ala Tyr Arg Arg Ala
1               5                   10                  15
Arg (2) INFORMATION FOR SEQ ID NO:6:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:6:

Lys Trp Leu Phe Arg Val Asn Tyr Arg Gly Ile Lys Tyr Arg Arg Gln
1               5                   10                  15

Arg ( 2 ) INFORMATION FOR SEQ ID NO:7:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:7:

```
Lys  Trp  Leu  Phe  Arg  Val  Thr  Tyr  Arg  Gly  Ile  Lys  Tyr  Arg  Arg  Gln
1                  5                        10                       15
Arg
```

( 2 ) INFORMATION FOR SEQ ID NO:8:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:8:

```
Lys  Trp  Leu  Arg  Val  Asn  Tyr  Arg  Gly  Ile  Lys  Tyr  Arg  Arg  Gln  Arg
1                  5                        10                       15
Gly  Ile  Gly  Ala  Val  Leu  Leu  Lys  Val  Leu  Thr  Thr  Gly
                   20                   25
```

( 2 ) INFORMATION FOR SEQ ID NO:9:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:9:

```
Lys  Trp  Leu  Phe  Arg  Val  Asn  Tyr  Arg  Gly  Ile  Lys  Tyr  Arg  Arg  Gln
1                  5                        10                       15
Arg  Gly  Ser  Thr  Ser  Gly  Gly  Ile  Gly  Ala  Val  Leu  Lys  Val  Leu  Thr
                   20                   25                       30
Thr  Gly  Leu
          35
```

( 2 ) INFORMATION FOR SEQ ID NO:10:

( i ) SEQUENCE CHARACTERISTICS:
        ( A ) LENGTH: 17 amino acids
        ( B ) TYPE: amino acid (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:10:

Lys Tyr Leu Phe Arg Val Asn Tyr Arg Gly Ile Lys Tyr Arg Arg Gln
    1               5                   10                  15
    Arg (2) INFORMATION FOR SEQ ID NO:11:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:11:

Lys Phe Leu Phe Arg Val Asn Tyr Arg Gly Ile Lys Tyr Arg Arg Gln
    1               5                   10                  15
    Arg (2) INFORMATION FOR SEQ ID NO:12:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:12:

Arg Tyr Leu Phe Arg Val Asn Tyr Arg Gly Ile Arg Tyr Arg Arg Gln
    1               5                   10                  15
    Arg (2) INFORMATION FOR SEQ ID NO:13:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:13:

Lys Tyr Gln Phe Arg Val Asn Tyr Arg Gly Ile Lys Tyr Arg Arg Gln
    1               5                   10                  15

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:14:

```
Arg Tyr Gln Phe Arg Val Asn Tyr Arg Gly Ile Lys Tyr Arg Arg Gln
 1               5                  10                  15
Arg
```

(2) INFORMATION FOR SEQ ID NO:15:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:15:

```
Lys Trp Leu Phe Arg Val Asn Tyr Arg Gly Ile Lys Tyr Arg Arg Gln
 1               5                  10                  15
Arg Lys Asp Glu Leu
                20
```

(2) INFORMATION FOR SEQ ID NO:16:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:16:

```
Lys Trp Cys Phe Arg Val Cys Tyr Arg Gly Ile Cys Tyr Arg Arg Cys
 1               5                  10                  15
Arg Gly Ser Thr Ser Gly Lys Trp Cys Phe Arg Val Cys Tyr Arg Gly
                20                  25                  30
Ile Cys Tyr Arg Arg Cys Arg
                35
```

(2) INFORMATION FOR SEQ ID NO:17:

(i) SEQUENCE CHARACTERISTICS:
        (A) LENGTH: 17 amino acids
        (B) TYPE: amino acid
        (C) STRANDEDNESS: single ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:17:

Lys Trp Cys Phe Lys Val Cys Tyr Arg Gly Ile Cys Tyr Lys Lys Cys
    1               5                   10                  15
    Lys ( 2 ) INFORMATION FOR SEQ ID NO:18:

( i ) SEQUENCE CHARACTERISTICS:
            ( A ) LENGTH: 17 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:18:

Lys Trp Lys Phe Arg Val Lys Tyr Arg Gly Ile Lys Tyr Arg Arg Lys
    1               5                   10                  15
    Arg ( 2 ) INFORMATION FOR SEQ ID NO:19:

( i ) SEQUENCE CHARACTERISTICS:
            ( A ) LENGTH: 17 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:19:

Lys Trp Leu Phe Arg Val Leu Tyr Arg Gly Ile Leu Tyr Arg Arg Leu
    1               5                   10                  15
    Arg ( 2 ) INFORMATION FOR SEQ ID NO:20:

( i ) SEQUENCE CHARACTERISTICS:
            ( A ) LENGTH: 13 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:20:

Lys Trp Leu Phe Arg Val Asn Lys Tyr Arg Arg Gln Arg
    1               5                   10

( 2 ) INFORMATION FOR SEQ ID NO:21:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:21:

```
Lys  Trp  Arg  Phe  Arg  Val  Arg  Tyr  Arg  Gly  Ile  Glu  Tyr  Arg  Arg  Glu
 1                   5                        10                       15
Arg
```

1

DERIVATIVES OF TACHYPLESIN HAVING INHIBITORY ACTIVITY TOWARDS PLANT PATHOGENIC FUNGI

TECHNICAL FIELD

This invention relates to compositions and methods for killing fungi which are harmful to plants, and materials and methods for imparting disease resistance to plants.

BACKGROUND OF THE INVENTION

Numerous fungi and bacteria are serious pests of common agricultural crops. One method of controlling diseases has been to apply antimicrobial organic or semiorganic chemicals to crops or seeds. This method has numerous, art-recognized problems. A more recent method of controlling pathogenic microorganisms has been the use of biological control organisms which are typically natural competitors or inhibitors of the troublesome microorganisms. However, it is difficult to apply biological control organisms to large areas, and even more difficult to assure that those living organisms will persist in the treated area for an extended period. Still more recently, techniques in recombinant DNA have provided the opportunity to insert into plant cells cloned genes which express peptides of interest, some of which are antimicrobial. This technology has given rise to additional concerns about eventual microbial resistance to well-known, naturally occurring antimicrobials, particularly in the face of heavy selection pressure, which may occur in some areas. Thus, a continuing need exists to identify naturally occurring antimicrobial compounds which can be formed by plant cells, either directly or indirectly, by translation of a single structural gene.

European Patent Application 204,590, based upon U.S. patent application Ser. No. 725,368, describes a method of genetically modifying a plant cell to control expression of heterologous foreign structure genes. In the method, the plant cell is transformed to contain a pRi T-DNA promoter and a heterologous foreign structural gene, the promoter and the structural gene being in such position and orientation with respect to one another that the structural gene is expressible in a plant cell under control of the promoter.

Likewise, European Patent Application 186,425, based upon U.S. patent application Ser. No. 685,824, describes a recombinant DNA expression vector which comprises (a) a transcription unit, flanked by T-DNA border sequences, which comprises a promoter and associated amino terminal region encoding sequences and a terminator signal sequence in which the sequences are derived from one or more genes which are naturally expressed in a plant cell, and (b) an antibiotic resistance gene-encoding sequence located between the promoter and associated amino-terminal region-encoding sequence and the terminator sequence and (c) a DNA fragment containing a replicon that is functional in Agrobacterium.

PCT application 8807087, based upon U.S. patent application Ser. No. 168,109, discloses a recombinant virus expression system comprising a Heliothis polyhedrin promoter and a nucleotide sequence encoding a heterologous peptide or protein, which may have antimicrobial activity.

Akaji, K. et al., *Chem. Pharm. Bull. (Tokyo)* 37(10):2661–2664 (1989), reports is the syntheses of three peptides from horseshoe crab, including tachyplesin I and II.

Kawano, K. et al., *J. Biol. Chem.* 265(26):15365–15367 (1990), reports the isolation of tachyplesin I from hemocytes of the horseshow crab, and determination of its beta-sheet structure.

Miyata, T. et al., *J. Biochem (Tokyo)* 106(4):663–669 (1989), discloses isolation of tachyplesin II from horseshoe crab and elucidation of its structure and biological activity.

Muta, T. et al., *J. Biochem (Tokyo)* 108(2):261–266 (1990), discloses isolation of tachyplesin III and a processing intermedate of its precursor.

Nakamura, T. et al., *J. Biol. Chem.* 263(32):16709–16713 (1988), discusses isolation and chemical structure of tachyplesin.

Niwa, M. et al., *First Scientific Meeting of the Japanese Association for Developmental and Comparative Immunology (Jadci)*, Tokyo, Japan, November (14(2):2–3 (1990) deals with the antimicrobial activities of tachyplesin isopeptides.

Shieh, T. C. et al., *FEBS (Fed. Eur. Biochem. Soc.) Lett.* 252(1–2):121–124 (1989) discloses synthesis and properties of tachyplesin I.

Shigenaga, T. et al., *J. Biol. Chem..* 265(34):21350–21354 (1990) describes cloning of cDNA for the peptide precursor of tachyplesin and the cellular localization of the peptide in the horseshoe crab.

Japanese laid-open patent application 02207098, assigned to Taiyo Fishery KK, disloses a composition having high specificity to beta-glucan. The composition includes an amoebocyte lysate from Lumulina and blood cell membrane proteins including tachyplesins I and II.

Japanese laid-open patent application 02204500, also assigned to Taiyo Fishery KK, discloses an article insoluble carrier for removing pyrogens from fluids. The article is made by bonding crab peptides identified as tachyplesins I and II to a water-insoluble carrier.

Prior copending, commonly assigned application Ser. No. 07/802,794, filed Dec. 6, 1991, "Peptide with Inhibitory Activity Towards Plant Pathogenic Fungi", the European counterpart of which was published Jun. 6, 1993, relates to the discovery that tachyplesins also have activity against fungal pathogens of common crop plants.

The disclosures of the foregoing references are hereby incorporated herein in their entirety by reference to show the state of the art.

DISCLOSURE OF THE INVENTION

It has now been determined that certain specific derivatives of the peptide tachyplesin have potent antifungal activity against common plant pathogens. Tachyplesin is a small peptide originally isolated from the hemocytes of the horseshoe crab, *Tachypleus tridentatus*. The native peptide has 17 amino acids, six of which are cysteines. Tachyplesin's conformation consists of an antiparallel β-sheet connected by a β-turn. Five bulky hydrophobic side groups are localized on one side of the plane and six cationic side groups are distributed at the tail part of the molecule.

The compounds of this invention have amino acid sequences indicated in the Sequence Listing as Sequence I.D. Nos. 1 through 3 and 5 through 14. In single-letter code preferred by biochemists, they are KWLFRVNGSSGKYRRQR (SEQUENCE I.D. NO. 1), KWLFRVNFRGIKYRRQR (SEQUENCE I.D. NO. 2), KWLFRVNQLMFKYRRQR (SEQUENCE I.D. NO. 3), KWAFRVAYRGIAYRRAR (SEQUENCE I.D. NO. 5) KWLFRVNYRGIKYRRQR (SEQUENCE I.D. NO 6), KWLFRVTYRGIKYRRQR (SEQUENCE I.D. NO. 7), KWLRVNYRGIKYRRQRGIGAVLLKVLTTG (SEQUENCE I.D. NO. 8), KWLFRVNYRGIKYRRQRGSTSGGIGAVLKVLTTGL (SEQUENCE I.D. NO. 9), KYLFRVNYRGIKYRRQR (SEQUENCE I.D. NO. 10), KFLFRVNYRGIKYRRQR (SEQUENCE I.D. NO. 11), RYLFRVNYRGIRYRRQR (SEQUENCE I.D. NO. 12), KYQFRVNYRGIKYRRQR (SEQUENCE I.D. NO. 13), RYQFRVNYRGIKYRRQR (SEQUENCE I.D. NO. 14), KWLFRVNYRGIKYRRQRKDEL (SEQUENCE I.D. NO. 15), KWCFRVCYRGICYRRCRGSTSGKWCFRVCYRGICYRRCR (SEQUENCE I.D. NO. 16), KWCFKVCYRGICYKKCK (SEQUENCE I.D. NO. 17), KWKFRVKYRGIKYRRKR (SEQUENCE I.D. NO. 18), KWLFRVLYRGILYRRLR (SEQUENCE I.D. NO. 19), KWLFRVNKYRRQR (SEQUENCE I.D. NO. 20), and KWRFRVRYRGIEYRRER (SEQUENCE I.D. NO. 21), respectively. SEQUENCE I.D. NO. 4 is natural tachyplesin, with the sequence KWCFRVCYRGICYRRCR. All sequences are indicated in the amino-to-carboxy direction.

These peptides are particularly active against the following group of plant pathogenic fungi and seed pathogens: *Fusarium graminearum, Fusarium moniliforme, Sclerotinia sclerotiorum, Sclerotinia trifoliorum,* and *Aspergillus flavus*. All of these fungi have significant economic impact. They produce crop losses through ear mold damage, and are also responsible for contamination of grain with aflatoxins and fumonisins.

Thus, this invention provides a method for killing and/or inhibiting susceptible plant pathogens, including microorganisms selected from the group listed above comprising the step of introducing into the environment of the organisms an antimicrobial amount of one or more peptides of this invention. "Killing" is meant here in the usual sense and "inhibiting" is used here in the sense commonly understood in antimicrobial susceptibility testing, namely, a reduction in growth and/or reproduction of the microorganism according to standard measurements, such as the Minimum Inhibitory Concentration, or MIC. Reference may be had to standard published texts, such as *Antimicrobial Susceptibility Testing*, 3rd Ed., written by the staff of the National Committee for Clinical Laboratory Standards (1991) and the multivolume set *Performance Standards for Antimicrobial Susceptibility Tests* published by the same group; and *Manual of Clinical Microbiology*, 5th ed., Balows, A. et al. Eds., pp. 1059–1202 (American Society for Microbiology, Washington, D.C., 1991) the disclosures of all of which are hereby incorporated by reference in their entirety.

These compounds can be effectively applied to plants infested with the microorganisms by spray, dust or other formulation common to the antimicrobial arts. Alternatively, the peptide can be incorporated into the tissues of a susceptible plant so that in the course of infesting the plant the pathogens will be exposed to antimicrobial amounts of the peptide. Known methods of doing this are to incorporate the peptide in a non-phytotoxic vehicle which is adapted for systemic administration to the susceptible plants, such as an endophytic bacterium or a lipid vesicle or microsphere.

See, for example, U.S. Pat. No. 5,157,207, issued Oct. 20, 1992 to Carlson, et al., the disclosures of which are hereby incorporated by reference, directed to modified plants containing bacterial inoculants. According to the '207 patent, certain types of microorganisms, such as hybrid agricultural-chemical-producing endosymbiotic microorganisms, can colonize the interior of plants and provide useful agricultural chemicals, such as pesticides, to the plants. Certain microbial endophytes are capable of inducing enhanced resistance in a host to phytopathogens. The bacteria that are suitable for use in such a method in this invention belong to a species of bacteria that is capable of replicating in the interior tissues of a plant and of producing the desired compound of this invention. Under normal field conditions, the bacterium does not ordinarily inhabit the seed or the plant into which the bacterium is introduced. Such a bacterium can be a gram-positive bacterium, a gram-negative bacterium or a species of actinomycetes. The bacterium is modified by genetic engineering techniques to incorporate the gene coding for the compound of this invention. In a preferred embodiment, the bacterial cell is a genetically modified species of either Corynebacteria, Clavibacter, Pseudomonas, Xanthomonas or Erwinia, the corynebacteria and clavibacters being as defined in Davis M. J. et al. (1984), loc. cit. In a particularly preferred embodiment, the bacterial cell is a strain of *Clavibacter xyli*. In a most preferred embodiment, the bacterial cell is a *Clavibacter xyli* subspecies *cynodontis*.

Reference also may be had to U.S. Pat. No. 5,252,348, issued Oct. 12, 1993 and directed to "Artificial viral envelopes", the disclosures of which are also hereby incorporated herein by reference. According to the '348 patent, lipid vesicles of the patent can be used to transfer biological material to plant cells.

Further reference may be had to U.S. Pat. No. 5,071,654, issued Dec. 10, 1991, the disclosures of which are hereby incorporated by reference and which are directed to insecticidal compositions involving a phospholipid vesicle with insect midgut brush border and a *Bacillus thuringiensis* protein endotoxin incorporated therein and an agriculturally-acceptable carrier. Such phospholipid vesicle compositions are stated to provide a vehicle for the application of delta endotoxin to plants. The vesicles are stated to act in much the same fashion as liposomes do in vertebrates, to facilitate the delivery of the toxins to the target midgut cells in susceptible insects.

Reference may also be had to U.S. Pat. No. 5,034,322, issued Jul. 23, 1991 to Rogers, et. al., the disclosures of which are hereby incorporated by reference and which are directed to chimeric genes suitable for expression in plant cells, but which discusses methods capable of inserting the chimeric genes of this invention into plant cells, although the reported transformation efficiencies achieved to date by such methods have been low. Discussed methods include use of lipid vesicles, also called liposomes, from which DNA may be taken up by plant cells.

Still further reference may be had to U.S. Pat. No. 4,588,578, issued May 13, 1986 to Fountain, et. al. and directed to monophasic vesicles for delivery of antimicrobials and other compounds to plants, and U.S. Pat. No. 4,522,803, issued Jun. 11, 1985 to Lenk, et. al. and directed, inter alia, to methods for treatment of infections in plants, comprising administering stable plurilamellar vesicles containing a compound effective for treating said infection. The disclosures of these patents are also hereby incorporated by reference.

The foregoing and similar methods are commonly employed with insecticidal materials which are designed to attack chewing insects and are well within the purview of one of ordinary skill in the art of insecticide and larvicide formulation and are fully contemplated in the practice of this invention. However, genes which code for the peptides of this invention can be readily synthesized using automated methods, cloned, inserted into an appropriate expression cassette, and introduced directly into cells of a susceptible plant species. Accordingly, an especially preferred embodiment of this method involves inserting into the genome of the plant a DNA sequence coding for one or more of the peptides of this invention in proper reading frame, together with transcription initiator and promoter sequences active in the plant. Transcription and translation of the DNA sequence(s) trader control of the regulatory sequences causes expression of the peptide sequence(s) at levels which provide an antimicrobial amount of the peptide(s) in the tissues of the plant which are normally infected by the pathogens.

With a working knowledge of conventional techniques for cloning, DNA isolation, amplification and purification, for enzymatic reactions involving DNA ligase, DNA polymerase, restriction endonucleases and the like, and various separation techniques known and commonly employed by those skilled in the art (See, for example, R. Wu, ed. (1979) *Meth. Enzymol.* 68; R. Wu et al., eds. (1983) *Meth. Enzymol.* 100, 101: L. Grossman and K. Moldave, eds. (1980) *Meth. Enzymol.* 65: J. H. Miller (1972) Experiments in Molecular Genetics; R. Davis et al. (1980) *Advanced Bacterial Genetics;* R. F. Schleif and P. C. Wensink (1982) *Practical Methods in Molecular Biology;* and T. Manniatis et al. (1982) *Molecular Cloning.*), one of ordinary skill can employ any suitable gene construct containing the structural genes coding for the peptides of this invention.

The plant is preferably a plant susceptible to infection and damage by one or more of *Fusarium graminearum, Fusarium moniliforme, Sclerotinia sclerotiorum, Sclerotinia trifoliorum,* or *Aspergillus flavus.* These include corn (*Zea mays*) and sorghum (*Sorghum bicolor*). However, this is not to be construed as limiting, inasmuch as these species are among the most difficult commercial crops to reliably transform and regenerate, and these microorganisms also infect many other crops. Thus the methods of this invention are readily applicable via conventional techniques to numerous plant species, if they are found to be susceptible to the plant pests listed hereinabove, including, without limitation, species from the genera Allium, Antirrhinum, Arabidopsis, Arachis, Asparagus, Atropa, Avena, Beta, Brassica, Browallia, Capsicum, Cicer, Cicla, Citrullus, Citrus, Cucumis, Cucurbita, Datura Daucus, Digitalis, Fagopyrum, Fragaria, Geranium, Glycine, Gossypium, Helianthus, Hordeum, Hemerocallis, Lactuca, Lens, Lolium, Lotus, Lycopersicon, Majorana, Manihot, Medicago, Nasturtium, Nicotiana, Oryza, Pelargonium, Persea, Petunia, Phaseolus, Pisum, Ranunculus, Raphanus, Ricinus, Saccharum, Secale, Senecio, Setaria, Solanum, Spinacia, Trifolium, Triticum, Bromus, Cichorium, Hyoscyamus, Linum, Nemesia, Panicum, Onobrychis, Pennisetum, Salpiglossis, Sinapis, Trigonella, and Vigna. Preferred plants that are to be transformed according to the methods of this invention are cereal crops, including maize, rye, barley, wheat, sorghum, oats, millet, rice, triticale, sunflower, alfalfa, rapeseed and soybean.

The DNA sequence which when expressed imparts antimicrobial activity is a structural gene which codes for at least one of the peptides of this invention. Given the amino acid sequences provided herein, any of several translationally equivalent synthetic DNA sequences can then be prepared which code for the sequences of amino acids using commercially available software, such as PC Gene™ or GCG™, and this synthetic sequence can be inserted into an appropriate plant expression cassette.

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong constitutive promoter sequence at one end to cause the gene to be transcribed at a high frequency, and a poly-A recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, La., as described in U.S. patent application Ser. No. 387,739, filed Aug. 1, 1989, and its continuation-in-part, Ser. No. 785,648, filed Oct. 31, 1991, the disclosures of which are hereby incorporated herein by reference in their entirety. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

According to this invention, the genetic construct will contain (a) a first genetic sequence coding for at least one peptide of this invention, and (b) one or more regulatory sequences operably linked on either side of the structural gene of interest. Typically, the regulatory sequences will be selected from the group comprising promoters and terminators. The regulatory sequences may be from autologous or heterologous sources.

Promoters that may be used in the genetic sequence include nos, ocs, napin, phaseolin and CaMV promoters, as well as others specifically discussed herein.

An efficient plant promoter that may be used is an overproducing plant promoter. Overproducing plant promoters that may be used in this invention include the promoter of the small sub-unit (ss) of the ribulose-1,5-biphosphate carboxylase from soybean (Berry-Lowe et al, *J. Molecular and App. Gen.,* 1:483–498 (1982)), and the promoter of the cholorophyll a-b binding protein. These two promoters are known to be light-induced in eukaryotic plant cells (see, for example, *Genetic Engineering of Plants, An Agricultural Perspective,* A. Cashmore, Pelham, N.Y., 1983, pp. 29–38, G. Coruzzi et al., *J. Biol. Chem.,* 258:1399 (1983), and P. Dunsmuir, et al., *J. Molecular and App. Gen.,* 2:285 (1983)).

The expression cassette comprising the structural gene for one or more peptides of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the antimicrobial peptide gene can be isolated in significant quantifies for introduction into the desired plant cells. Host cells that can be used in the practice of this invention include prokaryotes, including bacterial hosts such as *E. coli, S. typhimurium,* and *Serratia marcescens.* Eukaryotic hosts such as yeast or filamentous fungi may also be used in this invention. Since these hosts are also microorganisms, it will be essential to ensure that plant promoters which do not cause expression of the peptide in bacteria are used in the vector, or that a host microorganism which is resistant to is used. However, a particular benefit of the peptides of this invention is their relatively low toxicity to common bacterial hosts such as *E. coli* and *Agrobacterium tumefaciens.* By comparison, tachyplesin shows significant toxicity to *E. coli* even at the lowest effective antifungal concentrations.

The isolated cloning vector will then be introduced into the plant cell using any convenient technique, including electroporation (in protoplasts), retroviruses, bombardment, and microinjection, into cells from monocotyledonous or dicotyledonous plants, in cell or tissue culture, to provide transformed plant cells is containing as foreign DNA at least one copy and preferably more than one copy of the DNA sequence of the plant expression cassette. Preferably, the monocotyledonous species will be selected from maize, sorghum, wheat and rice, and the dicotyledonous species will be selected from soybean, alfalfa, tobacco and tomato. Using known techniques, protoplasts can be regenerated and cell or tissue culture can be regenerated to form whole fertile plants which carry and express the gene for one or more of the peptides of this invention. Accordingly, a highly preferred embodiment of the present invention is a transformed maize plant, the cells of which contain as foreign DNA at least one copy of the DNA sequence of an expression cassette of this invention as described above.

Finally, this invention provides methods of imparting resistance to diseases caused by microorganisms selected from *Fusarium graminearum, Fusarium moniliforme, Sclerotinia sclerotiorum, Sclerotinia trifoliorum,* and *Aspergillus flavus* to plants of a susceptible taxon, comprising the steps of:

a) culturing regenerable cells or tissues from at least one plant from the taxon, b) introducing into the cells of the cell or tissue culture at least one copy of an expression cassette comprising a gene which codes for at least one peptide of this invention, operably linked to plant regulatory sequences which cause the expression of peptide(s) in the cells, and c) regenerating disease-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the structural gene for the antimicrobial peptide and associated regulatory sequences via crossing and backcrossing. Such intermediate methods will comprise the further steps of a) sexually crossing the disease-resistant plant with a plant from the disease-susceptible taxon;

b) recovering reproductive material from the progeny of the cross; and c) growing disease-resistant plants from the reproductive material.

Where desirable or necessary, the agronomic characteristics of the susceptible is taxon can be substantially preserved by expanding this method to include the further steps of repetitively:

a) backcrossing the disease-resistant progeny with disease-susceptible plants from the susceptible taxon; and b) selecting for expression of antimicrobial activity (or an associated marker gene) among the progeny of the backcross, until the desired percentage of the characteristics of the susceptible taxon are present in the progeny along with the gene imparting antimicrobial activity.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into *Agrobacterium tumefaciens,* which can then be used to transfer the vector into susceptible plant cells, especially those from dicotyledonous species. Thus, this invention provides a method for imparting antimicrobial activity and disease resistance in *Agrobacterium tumefaciens*-susceptible dicotyledonous plants in which the expression cassette is introduced into the cells by infecting the cells with *Agrobacterium tumefaciens,* a plasmid of which has been modified to include a plant expression cassette of this invention.

HUMAN AND VETERINARY PHARMACEUTICAL USE

This invention also provides methods of treating and preventing infection by susceptible organisms in a human or lower animal host in need of such treatment, which method comprises administration to the human or lower animal host in need of such treatment a therapeutically effective amount of a polypeptide of this invention or a composition containing one or more of the polypeptides. The polypeptides of the present invention may be administered parenterally, by inhalation spray, rectally or topically in dosage unit formulations containing conventional nontoxic, pharmaceutically acceptable carriers, adjuvants and vehicles as desired. The term parenteral as used herein includes subcutaneous, intravenous, intramuscular, intraarticular and intrathecal injection and infusion techniques. As with other polypeptides, the polypeptides of this invention are not known to be active orally.

Total daily dose of the compounds of this invention administered to a host in single or divided doses may be in amounts, for example, of from 1 to 2000 mg/kg body weight daily and more usually 50 to 500 mg/kg. Dosage unit compositions may contain such amounts or fractions or submultiples thereof as appropriate to make up the daily dose. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

This invention also provides pharmaceutical compositions in unit dosage form, comprising an effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cottonseed oil, safflower oil, sesame oil, olive oil, corn oil and soybean oil; polyols such as propylene glycol, glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other non-toxic compatible substances used s in pharmaceutical formulations. Wetting agents, emulsifiers and lubricants such as sodium lauryl sulfate and magnesium stearate, as well as coloring agents, release agents, coating agents, and perfuming agents and preservatives can also be present in the compositions, according to the desires of the formulator. The amount of active ingredient that may be combined with the carrier materials to produce a single dosage form will vary depending upon the host treated and the particular mode of administration.

By "therapeutically effective amount" herein is meant an amount of either polypeptide or combination thereof sufficient to provide antifungal activity so as to alleviate or prevent infection by susceptible organisms in the human or lower is animal being treated at a reasonable benefit/risk ratio attendant with any medical treatment.

The following description further exemplifies the compositions of this invention and the methods of making and using them. However, it will be understood that other methods, known by those of ordinary skill in the art to be equivalent, can also be employed.

INDUSTRIAL APPLICABILITY

EXAMPLE 1

Antifungal Testing

Peptide samples for this and the other Examples were synthesized from the predetermined amino acid sequence and structure, according to methods reported in the literature, specifically the "Fastmoc" method described by C. G. Fields, et al., *Peptide Res.*, Vol. 4 pp.95–101 (1991). Since the peptides of this invention are new but the methods of their synthesis are routine, the methods of synthesis per se are not considered a part of this invention.

Minimum Inhibitory Concentrations (MIC) and Minimum Complete Inhibitory Concentrations (MCIC) in μg/mL were determined for each of the compounds of this invention using the published methods of Duvick, J. P. et al, *J. Biol. Chem.*, 267, 18814–18820 (1992). Results were as follows:

| Fungus | MIC | MCIC |
|---|---|---|
| SEQUENCE I.D. NO. 1 | | |
| *Aspergillus flavus* | 60 | >80 |
| *Fusarium graminearum* | 20 | 60 |
| *Fusarium moniliforme* | 10 | 40 |
| SEQUENCE I.D. NO. 2 | | |
| *Aspergillus flavus* | 20 | >80 |
| *Fusarium graminearum* | 20 | 40 |
| *Fusarium moniliforme* | 10 | 20 |
| SEQUENCE I.D. NO. 3 | | |
| *Aspergillus flavus* | 5 | 60 |
| *Fusarium graminearum* | 10 | 10 |
| *Fusarium moniliforme* | 2.5 | 10 |
| SEQUENCE I.D. NO. 5 | | |
| *Aspergillus flavus* | NA | NA |
| *Fusarium graminearum* | NA | NA |
| *Fusarium moniliforme* | NA | NA |
| SEQUENCE I.D. NO. 6 | | |
| *Aspergillus flavus* | 38 | 61 |
| *Fusarium graminearum* | 25 | 48 |
| *Fusarium moniliforme* | 16 | 48 |
| SEQUENCE I.D. NO. 7 | | |
| *Aspergillus flavus* | 40 | >80 |
| *Fusarium graminearum* | 20 | 30 |
| *Fusarium moniliforme* | 20 | 40 |
| SEQUENCE I.D. NO. 8 | | |
| *Aspergillus flavus* | 38 | >80 |
| *Fusarium graminearum* | 13 | 18 |
| *Fusarium moniliforme* | 13 | 35 |
| SEQUENCE I.D. NO. 9 | | |
| *Aspergillus flavus* | NA | NA |
| *Fusarium graminearum* | 40 | 80 |
| *Fusarium moniliforme* | 40 | >80 |
| SEQUENCE I.D. NO. 10 | | |
| *Aspergillus flavus* | 50 | >80 |
| *Fusarium graminearum* | 22 | 58 |
| *Fusarium moniliforme* | 20 | 63 |
| SEQUENCE I.D. NO. 11 | | |
| *Aspergillus flavus* | 40 | >80 |
| *Fusarium graminearum* | 40 | 80 |
| *Fusarium moniliforme* | 20 | 80 |
| SEQUENCE I.D. NO. 12 | | |
| *Aspergillus flavus* | NA | NA |
| *Fusarium graminearum* | 80 | >80 |
| *Fusarium moniliforme* | 80 | >80 |
| SEQUENCE I.D. NO. 13 | | |
| *Aspergillus flavus* | 28 | 200 |
| *Fusarium graminearum* | 32 | 58 |
| *Fusarium moniliforme* | 13 | 68 |
| SEQUENCE I.D. NO. 14 | | |
| *Aspergillus flavus* | 35 | 200 |
| *Fusarium graminearum* | 32 | 68 |
| *Fusarium moniliforme* | 18 | 68 |
| SEQUENCE I.D. NO. 15 | | |
| *Aspergillus flavus* | 80 | >80 |
| *Fusarium graminearum* | 30 | 80 |
| *Fusarium moniliforme* | 30 | >80 |
| SEQUENCE I.D. NO. 16 | | |
| *Aspergillus flavus* | 32 | >64 |
| *Fusarium graminearum* | 12 | 32 |
| *Fusarium moniliforme* | 16 | 64 |

| Fungus | MIC | MCIC |
|---|---|---|
| SEQUENCE I.D. NO. 17 | | |
| Aspergillus flavus | 25 | 93 |
| Fusarium graminearum | 7.5 | 25 |
| Fusarium moniliforme | 12 | 48 |
| SEQUENCE I.D. NO. 18 | | |
| Aspergillus flavus | 20 | >80 |
| Fusarium graminearum | 10 | 20 |
| Fusarium moniliforme | 5 | 20 |
| SEQUENCE I.D. NO. 19 | | |
| Aspergillus flavus | 60 | >80 |
| Fusarium graminearum | 10 | 80 |
| Fusarium moniliforme | 3.75 | 80 |
| SEQUENCE I.D. NO. 20 | | |
| Aspergillus flavus | 20 | 80 |
| Fusarium graminearum | 20 | 40 |
| Fusarium moniliforme | 10 | 40 |
| SEQUENCE I.D. NO. 21 | | |
| Aspergillus flavus | 20 | 80 |
| Fusarium graminearum | 20 | 20 |
| Fusarium moniliforme | 10 | 40 |

In these tables, NA = not active.

For comparison, tachyplesin and other known antimicrobial compounds have MICs as follows:

| Protein | MIC μg/ml (μM) | | |
|---|---|---|---|
| | AFL | FGR | FMO |
| tachyplesin | 6.25 (2.8) | 6.25 (2.8) | 6.25 (2.8) |
| defensin | 11.7 (3) | 2.6 (0.7) | 11.7 (3) |
| hordothionin | 15 (3) | 5 (1) | 45 (9) |
| CMIII | 60 (15) | 6.2 (1.6) | 18.2 (4.6) |

EXAMPLE 2

Antibacterial Testing

Minimum Inhibitory Concentrations (MIC) and Minimum Complete Inhibitory Concentrations (MCIC) in μg/mL against selected species of bacteria were determined for each of the compounds of this invention. Results were as follows:

| Bacterium | MIC | MCIC |
|---|---|---|
| SEQUENCE I.D. NO. 1 | | |
| E. coli | 6.25 | >100 |
| E. stewartii | 6.25 | >100 |
| LBA 4404 | 50 | >100 |
| C. nebraskense | 3.13 | 25 |
| B. pumillus | >100 | |
| SEQUENCE I.D. NO. 2 | | |
| E. coli | 6.25 | >100 |
| E. stewartii | 6.25 | >100 |
| LBA 4404 | 6.25 | 25 |
| C. nebraskense | 6.25 | 12.5 |
| B. pumillus | 25 | >100 |
| SEQUENCE I.D. NO. 3 | | |
| E. coli | 3.13 | >100 |
| E. stewartii | 3.13 | >100 |
| LBA 4404 | 50 | 100 |
| C. nebraskense | nt | |
| B. pumillus | 12.5 | >100 |
| SEQUENCE I.D. NO. 5 | | |
| E. coli | nt | |
| E. stewartii | nt | |
| LBA 4404 | nt | |
| C. nebraskense | nt | |
| B. pumillus | nt | |
| SEQUENCE I.D. NO. 6 | | |
| E. coli | 100 | >100 |
| E. stewartii | 6.25 | >100 |
| LBA 4404 | 6.25 | 50 |
| C. nebraskense | 6.25 | 12.5 |
| B. pumillus | 50 | >100 |
| SEQUENCE I.D. NO. 7 | | |
| E. coli | 100 | >100 |
| E. stewartii | 6.25 | >100 |
| LBA 4404 | 50 | 100 |
| C. nebraskense | 6.25 | 25 |
| B. pumillus | 25 | >100 |
| SEQUENCE I.D. NO. 8 | | |
| E. coli | 25 | >100 |
| E. stewartii | 6.25 | >100 |
| LBA 4404 | 6.25 | >100 |
| C. nebraskense | 6.25 | 12.5 |
| B. pumillus | 50 | >100 |
| SEQUENCE I.D. NO. 9 | | |
| E. coli | 12.5 | >100 |
| E. stewartii | 12.5 | >100 |
| LBA 4404 | 100 | >100 |
| C. nebraskense | 12.5 | 12.5 |
| B. pumillus | 50 | >100 |
| SEQUENCE I.D. NO. 10 | | |
| E. coli | 100 | >100 |
| E. stewartii | 6.25 | >100 |
| LBA 4404 | 25 | 100 |
| C. nebraskense | 12.5 | 12.5 |
| B. pumillus | 50 | >100 |
| SEQUENCE I.D. NO. 11 | | |
| E. coli | 50 | >100 |
| E. stewartii | 6.25 | >100 |
| LBA 4404 | 12.5 | >100 |
| C. nebraskense | 12.5 | 12.5 |
| B. pumillus | 100 | >100 |
| SEQUENCE I.D. NO. 12 | | |
| E. coli | 100 | >100 |
| E. stewartii | 12.5 | >100 |
| LBA 4404 | nt | nt |
| C. nebraskense | nt | nt |
| B. pumillus | nt | nt |
| SEQUENCE I.D. NO. 13 | | |
| E. coli | 50 | >100 |
| E. stewartii | 3.13 | >100 |
| LBA 4404 | 50 | >100 |
| C. nebraskense | 6.25 | >100 |
| B. pumillus | 6.25 | 100 |
| SEQUENCE I.D. NO. 14 | | |
| E. coli | 100 | >100 |
| E. stewartii | 6.25 | >100 |
| LBA 4404 | 3.13 | >100 |
| C. nebraskense | 6.25 | 100 |
| B. pumillus | 6.25 | >100 |
| SEQUENCE I.D. NO. 15 | | |
| E. coli | 50 | >100 |
| E. stewartii | 6.25 | 50 |
| LBA 4404 | 6.25 | >100 |
| C. nebraskense | 50 | >100 |
| B. pumillus | 50 | >100 |

| Bacterium | MIC | MCIC |
|---|---|---|
| SEQUENCE I.D. NO. 17 | | |
| E. coli | 3.13 | >100 |
| E. stewartii | 3.13 | 25 |
| LBA 4404 | 3.13 | 12.5 |
| C. nebraskense | 3.13 | 25 |
| B. pumillus | 6.25 | 100 |
| SEQUENCE I.D. NO. 18 | | |
| E. coli | 6.25 | 25 |
| E. stewartii | 6.25 | 100 |
| LBA 4404 | 50 | >100 |
| C. nebraskense | 6.25 | 6.25 |
| B. pumillus | >100 | |
| SEQUENCE I.D. NO. 19 | | |
| E. coli | 3.13 | 50 |
| E. stewartii | 12.5 | 50 |
| LBA 4404 | 25 | 100 |
| C. nebraskense | 3.13 | 12.5 |
| B. pumillus | 100 | >100 |
| SEQUENCE I.D. NO. 20 | | |
| E. coli | 3.13 | 3.13 |
| E. stewartii | 12.5 | 50 |
| LBA 4404 | 50 | 50 |
| C. nebraskense | 6.25 | 25 |
| B. pumillus | 100 | >100 |
| SEQUENCE I.D. NO. 21 | | |
| E. coli | 6.25 | 25 |
| E. stewartii | 6.25 | 12.5 |
| LBA 4404 | 25 | 50 |
| C. nebraskense | 3.13 | 25 |
| B. pumillus | >100 | |

What is claimed is:

1. A peptide having the amino acid sequence of one of Sequence I.D. Nos. 1 through 3 or 6 through 21.

2. A method for killing and inhibiting fungi comprising introducing into the environment of the fungi an antimicrobially effective amount of at least one of the peptides having the amino acid sequence of one of Sequence I.D. Nos. 1 through 3 or 6 through 21.

3. A method according to claim 2 for killing and inhibiting fungal plant pathogens selected from *Fusarium graminearum, Fusarium moniliforme, Sclerotinia sclerotiorum, Sclerotinia trifoliorum,* and *Aspergillus flavus.*

4. A method according to claim 3 wherein the environment of the pathogen is the tissues of a living plant.

5. An antimicrobial composition for application to plants, comprising an antimicrobially effective amount of at least one peptide having the amino acid sequence of SEQUENCE I.D. NOS. 1 through 3 or 6 through 21, in a non-phytotoxic vehicle.

6. A composition according to claim 5 wherein the non-phytotoxic vehicle is adapted for systemic administration to a plant.

\* \* \* \* \*